(12) United States Patent
Pan et al.

(10) Patent No.: US 7,627,428 B2
(45) Date of Patent: Dec. 1, 2009

(54) METHOD OF EVALUATING SURFACE DEFORMATION

(75) Inventors: Ernian Pan, Macedonia, OH (US); Michael Bevis, Columbus, OH (US); Feng Han, Bellevue, WA (US); Hao Zhou, Columbus, OH (US); Ronghua Zhu, Akron, OH (US)

(73) Assignee: The University of Akron, Akron, OH (US)

( * ) Notice: Subject to any disclaimer, the term of this patent is extended or adjusted under 35 U.S.C. 154(b) by 197 days.

(21) Appl. No.: 11/933,862

(22) Filed: Nov. 1, 2007

(65) Prior Publication Data

US 2008/0177483 A1 Jul. 24, 2008

Related U.S. Application Data

(60) Provisional application No. 60/855,896, filed on Nov. 1, 2006.

(51) Int. Cl.
*G01L 1/00* (2006.01)

(52) U.S. Cl. ............... 702/5; 702/2; 702/14; 702/42

(58) Field of Classification Search ............... None
See application file for complete search history.

(56) References Cited

U.S. PATENT DOCUMENTS

| | | | |
|---|---|---|---|
| 5,327,561 A | 7/1994 | Choi et al. | |
| 5,534,875 A | 7/1996 | Diefes et al. | |
| 5,583,513 A | 12/1996 | Cohen et al. | |
| 5,614,670 A | 3/1997 | Nazarian et al. | |
| 6,028,819 A | 2/2000 | Mullarkey et al. | |
| 6,097,345 A | 8/2000 | Walton | |
| 6,138,075 A | 10/2000 | Yost | |
| RE37,256 E | 7/2001 | Cohen et al. | |
| 6,401,540 B1 | 6/2002 | Deason et al. | |

OTHER PUBLICATIONS

Agarwal, B.D. and Broutman, L.J. (1980): Analysis and Performance of Fiber Composites. John Wiley & Sons, New York.

Balaban, N.Q., Schwarz, U.S., Riveline, D., Goichberg, P., Tzur, G., Sabanay, I., Mahalu, D., Safran, S., Bershadsky, A., Addadi, L., and Geiger, B. (2001): Force and focal a adhesion assembly: a close relationship studied using elastic micropatterned substrates. Nature Cell Biology, 3, 466-472.

Becker, J.M. and Bevis, M. (2004): Love's problem. Geophys. J. Int. 156, 171-178.

(Continued)

*Primary Examiner*—Drew A Dunn
*Assistant Examiner*—Hien X Vo
(74) *Attorney, Agent, or Firm*—Roetzel and Andress; Joseph J. Crimaldi

(57) ABSTRACT

The present invention generally relates to methods for rapidly calculating the surface displacement that results from an arbitrarily shaped load on the surface of a layered substrate. Some embodiments include sparse direct calculations of surface displacement in combination with interpolation methods for estimating surface displacement at other points. Some embodiments include methods for reducing computer time required for calculating surface displacement caused by an arbitrarily shaped load on a layered surface.

4 Claims, 10 Drawing Sheets

OTHER PUBLICATIONS

Bevis, M., Kendrick, E., Cser, A., and Smalley, R. (2004): Geodetic measurement of the local elastic response to the changing mass of water in Lago Laja, Chile. Phys. Earth Planet. Inter. 141, 71-78.

Bimberg, D., Grundmann, M., and Ledentsov, N.V. (1999): Quantum Dot Heterostructures. John Wiley & Sons, New York.

Chave, A.D. (1983): Numerical integration of related Hankel transforms by quadrature and continued fraction expansion. Geophysics, 48, 1671-1686.

deBoor, C.R. (1979): A Practical Guide to Splines, Springer-Verlag, New York.

Gilbert, F. and Backus, G. (1966): Propagator matrices in elastic wave and vibration problems. Geophysics 31, 326-332.

Fukahaata, Y. and Matsu'ura, M. (2005): General expressions for internal deformation fields due to a dislocation source in a multilayered elastic half-space. Geophys. J. Int 161, 507-521.

Graig, R.F. (1997): Soil Mechanics. Taylor & Francis Group, London.

Khazanovich, L. (1994): Structural Analysis of Multi-Layered Concrete Pavement Systems. Ph.D. Thesis, University of Illinois, Urbana, IL.

Love, A.E.H. (1944): A Treatise on the Mathematical Theory of Elasticity. Fourth Edition, Dover Publications, New York.

Lucas, S.K. (1995): Evaluation infinite integrals involving products of Bessel functions of arbitrary order. J. Comput. Appl. Math. 64, 269-282.

Lucas, S.K. and Stone, H.A. (1995): Evaluations infinite integrals involving Bessel functions of arbitrary order. J. Comput. Appl. Math. 64, 217-231.

Murthy, V.N.S. (2003): Geotechnical Engineering: Principles and Practics of Soil Mechanics and Foundation Engineering. Marcel Dekker, Inc., New York.

Pan, E. (1989a): Static response of a transversely isotropic and layered half-space to general dislocation sources. Phys. Earth Planet. Inter. 58, 103-117.

Pan, E. (1989b): Static response of a transversely isotropic and layered half-space to general surface loads. Phys. Earth Planet. Inter. 54, 353-363.

Pan, E. (1997): Static Green's functions in multilayered half-spaces. Applied Mathematical Modelling 21, 509-521.

Pan, E and Han, F. (2004): Green's functions for transversely isotropic piezoelectric functionally graded multilayered half-spaces. J. Eng. Math. 49: 271-288.

Rice, J.R. (1983): Numerical Methods, Software, and Analysis: IMSL Reference Edition. McGraw-Hill Book Company, New York.

Wang, C.D., Tzeng, C.D., Pan, E. and Liao, J.J. (2003): Displacements and stresses due to a vertical point load in an inhomogeneous transversely isotropic half space. Int. J Rock Mech. Min. Sci. 40, 667-685.

Watson, G.N. (1996): A Treatise on the Theory of Bessel Functions. Cambridge University Press. Second Edition, Reprinted 1996.

Yue, Z.Q. And Yin, J.H. (1998): Backward transfer-matrix method for elastic analysis of layered solids with imperfect bonding. J. Elasticity 50, 109-128.

Pan, E. and Han, F. (2005): Green's functions for transversely isotropic piezoelectric functionally graded multilayered half spaces. International Journal of Solids and Structures, 42, 3207-3233.

METHOD OF EVALUATING SURFACE DEFORMATION

BACKGROUND OF THE INVENTION

The present invention is related to a process for calculating the surface displacement due to arbitrary vertical loads on the layered elastic half-space using a fast algorithm.

Evaluation of layered structures comes from the fact that structures with multiple layers are everywhere. Examples include superlattices in solid-state physics (Bimberg et al., 1999), composites in material science (Agarwal and Broutman, 1980), earth or foundation structures (or locally ground foundation) (Murthy, 2003), and layered pavements in highway transportation (Khazanovich, 1994). This in turn has motivated the corresponding analytical and numerical research aimed at both forward and inverse problems associated with layered structures (Wang et al., 2003; Pan and Han, 2005). However, even for the forward problems, namely the elastic response due to surface loading of the layered half-space, no fast method is available which can model complex surface loads.

The following references are background information and are incorporated herein by reference in their entirety:

Agarwal, B. D. and Broutman, L. J. (1980): *Analysis and Performance of Fiber Composites*. John Wiley & Sons, New York.

Balaban, N. Q., Schwarz, U.S., Riveline, D., Goichberg, P., Tzur, G., Sabanay, I., Mahalu, D., Safran, S., Bershadsky, A., Addadi, L., and Geiger, B. (2001): Force and focal adhesion assembly: a close relationship studied using elastic micropatterned substrates. *Nature Cell Biology*, 3, 466-472.

Becker, J. M. and Bevis, M. (2004): Love's problem. *Geophys. J. Int.* 156, 171-178.

Bevis, M., Kendrick, E., Cser, A., and Smalley, R. (2004): Geodetic measurement of the local elastic response to the changing mass of water in Lago Laja, Chile. *Phys. Earth Planet. Inter.* 141, 71-78.

Bimberg, D., Grundmann, M., and Ledentsov, N. N. (1999): *Quantum Dot Heterostructures*. John Wiley & Sons, New York.

Chave, A. D. (1983): Numerical integration of related Hankel transforms by quadrature and continued fraction expansion. *Geophysics* 48, 1671-1686.

de Boor, C. R. (1979): A Practical Guide to Splines, Springer-Verlag, New York.

Fukahata, Y. and Matsu'ura, M. (2005): General expressions for internal deformation fields due to a dislocation source in a multilayered elastic half-space. *Geophys. J. Int.* 161, 507-521.

Gilbert, F. and Backus, G. (1966): Propagator matrices in elastic wave and vibration problems. *Geophysics* 31, 326-332.

Graig, R. F. (1997): *Soil Mechanics*. Taylor & Francis Group, London.

Khazanovich, L. (1994): *Structural Analysis of Multi-Layered Concrete Pavement Systems*. Ph.D. Thesis, University of Illinois, Urbana, Ill.

Love, A. E. H. (1944): A Treatise on the Mathematical Theory of Elasticity. Fourth Edition, Dover Publications, New York.

Lucas, S. K. (1995): Evaluation infinite integrals involving products of Bessel functions of arbitrary order. *J. Comput. Appl. Math.* 64, 269-282.

Lucas, S. K. and Stone, H. A. (1995): Evaluating infinite integrals involving Bessel functions of arbitrary order. *J. Comput. Appl. Math.* 64, 217-231.

Murthy, V. N. S. (2003): *Geotechnical Engineering: Principles and Practices of Soil Mechanics and Foundation Engineering*. Marcel Dekker, Inc., New York.

Pan, E. (1989a): Static response of a transversely isotropic and layered half-space to general dislocation sources. *Phys. Earth Planet. Inter.* 58, 103-117.

Pan, E. (1989b): Static response of a transversely isotropic and layered half-space to general surface loads. *Phys. Earth Planet. Inter.* 54, 353-363.

Pan, E. (1997): Static Green's functions in multilayered half-spaces. *Applied Mathematical Modelling* 21, 509-521.

Pan, E. and Han, F. (2004): Green's functions for transversely isotropic piezoelectric multilayered half-spaces. *J. Eng. Math.* 49: 271-288.

Pan, E. and Han, F. (2005): Green's functions for transversely isotropic piezoelectric functionally graded multilayered half spaces. *International Journal of Solids and Structures*, 42, 3207-3233.

Rice, J. R. (1983): Numerical Methods, Software, and Analysis: IMSL Reference Edition. McGraw-Hill Book Company, New York.

Wang, C. D., Tzeng, C. S., Pan, E. and Liao, J. J. (2003): Displacements and stresses due to a vertical point load in an inhomogeneous transversely isotropic half-space. *Int. J. Rock Mech. Min. Sci.* 40, 667-685.

Watson, G. N. (1996): A Treatise on the Theory of Bessel Functions. Cambridge University Press. Second Edition, Reprinted 1996.

Yue, Z. Q. and Yin, J. H. (1998): Backward transfer-matrix method for elastic analysis of layered solids with imperfect bonding. *J. Elasticity* 50, 109-128.

SUMMARY OF THE INVENTION

The present invention generally relates to methods for rapidly calculating the surface displacement that results from an arbitrarily shaped load on a layered surface. Some embodiments include sparse direct calculations of surface displacement in combination with interpolation methods for estimating surface displacement at other points. Some embodiments include methods for reducing computer time required for calculating surface displacement caused by an arbitrarily shaped load on a layered surface.

The present invention also relates to process for calculating surface deformation, comprising providing a substrate having p layers; providing a load body having a contacting surface and the contacting surface is in contact with and disposed on the substrate and exerting a compressive load on the substrate; dividing the load body's contacting surface into a number L of circles each having an equal radius R; dividing the substrate into N stations located at the surface that is in contact with the loading body; selecting a desired maximum RMS relative error; selecting a number M of control points for forming a B-spline curve of the surface displacement of the stations; checking the expected error resulting from the number M of selected control points and comparing the expected error to the desired maximum RMS relative error; proceeding to a next step when the expected error is equal to or less than the desired maximum RMS relative error, or selecting more control points when the expected error is greater than the desired maximum RMS relative error; pre-calculating B-spline coefficients for a near field surface displacement, wherein the near field contains control points having spacing r, wherein r can have values between 0 and 2R, wherein the near field is defined by the range from 0 to 2R, wherein the near field is divided into three subsections defined by 0 to R−δ, R−δ to R+δ, and R+δ to 2R, wherein δ is between 0.02R and 0.1R, and wherein the distance between each control point is graded so that $|r_{i+1}-r_i|=g|r_i-r_{i-1}|$ and wherein g is between 1 and 2; pre-calculating B-spline coefficients for a middle field surface displacement, wherein the middle field contains control points having spacing r, wherein r can vary from 2R to 40R, wherein the middle field is defined by a range from 2R to 40R, wherein the control points are uniformly distributed in the middle field by a spacing defined according to the natural logarithmic function ln(r); pre-calculating inverse B-spline coefficients for a far field, wherein the far field contains control points having spacing 1/r, wherein r can vary from 40R to 100R, wherein the far field is defined by a range from 40R to 100R, wherein the control points are uniformly distributed according to the function 1/r; selecting coefficients and inverse coefficients from the pre-calculated coefficients and inverse coefficients, and forming a B-spline therefrom; interpolating according to the B-spline; and calculating station displacement for each station.

DETAILED DESCRIPTION OF THE INVENTION

The present invention relates to a process for computing surface responses due to arbitrary surface loading on a layered elastic half-space. The present invention also relates to such methods that are 2 to 3 orders of magnitude faster than existing methods. In some embodiments the process of the present invention provides a practical basis for least squares estimation of subsurface structural and elastic parameters based on observed surface responses to known surface loads. The load can be a force applied to the surface of the object being evaluated, and could include an ultrasonic force, or the like acoustic force, magnetic force, or similar mechanical loads or force. In some embodiments the process breaks an arbitrary surface load up into a large number L of small circular loading elements of equal radius R, and then reformulates the problem of computing the response at N stations in terms of a primitive and nearly equivalent problem: that of computing the response at L×N stations due to unit pressure loading applied within a single circle of radius R. Thus the problem is reduced to quickly solving a much simpler equation. Some embodiments exploit the fact that, for a single circular loading, the vertical and radial components of displacement depend only on the radial distance r from the center of the load. Therefore, great speed is achieved by sparse evaluation (using conventional methods) of the radial and vertical components of surface deformation at a set of control points located at various radial distances ($r_1, r_2, \ldots r_M$) from the center of the load, and interpolation to find the responses at intervening values of r. Hereinafter, the process of the present invention is referred to as the Sparse Evaluation and Massive Interpolation (SEMI) method. The SEMI method's speed arises from the fact that the product L×N is very large compared to the number of control points M.

Figure 10:
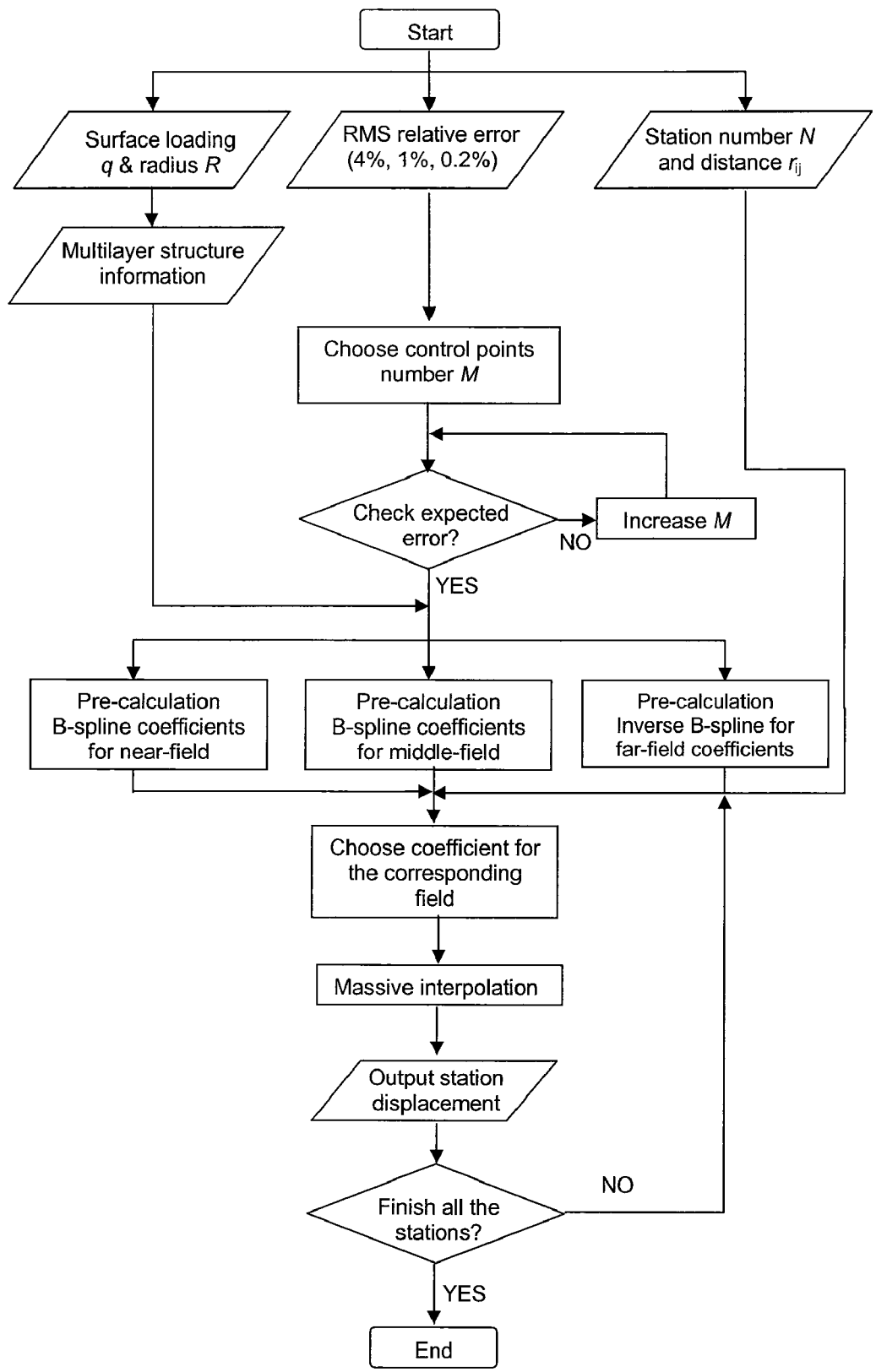
FIG. 10 is the flowchart of the SEMI method.

A non-limiting description of the SEMI method is shown in the flowchart in FIG. 10. A first step can include breaking up an arbitrarily shaped load body that contacts a layered substrate (i.e. the contact surface) into circular loading elements having radius R and uniform pressure q. The practitioner selects a desired RMS relative error (e.g. 4%, 1% or 0.2%). The practitioner selects positions on the layered substrate, referred to herein as stations, which are on the surface of the substrate. The practitioner then calculates a few test points according to the SEMI method, and compares the calculations to the direct method. If the RMS relative error is less than or equal to the desired relative error then no more control points are needed. If the relative error is greater than that which is desired then additional control points are selected, the error is re-checked. This process continues until the desired relative error is achieved. Then the B-spline coefficients for the near, middle and far fields are calculated. The B-splines are constructed and displacements are interpolated therefrom for each station. One of ordinary skill in the art will readily recognize that some of the steps set forth therein do not need to be performed in the order shown.

To illustrate the process of the present invention (i.e. SEMI), numerical examples are further provided where the surface response is divided into three sections with selected control points in each section. In some embodiments the surface response of interest is that which is due to a single circular loading element in the r-direction. Three different methods are proposed to pre-calculate the response in the three sections. Two typical layered examples are investigated with different number of selected control points. In some embodiments, it is observed that with only 20 pre-selected control points, the maximum RMS relative error in displacements between the direct and SEMI methods is less than 4%. Furthermore, the RMS relative error in displacement decreases inversely with respect to the power of the selected control point number M, at a speed faster than $1/M^3$. As such, when the number of selected control points is increased to 31, the maximum RMS relative error in displacements is reduced to less than 1%, and for 54 selected control points, the error is further reduced to less than 0.2%. Surprisingly, the process of the present invention is capable of keeping RMS relative error less than 0.2%, while at the same time being more than 1,200 times faster than the direct method. In part, this is due to the fact that the direct method calculates the response at 100,000 different surface stations for this example.

1. Statement of the Primitive Problem and Governing Equations

Figure 1:
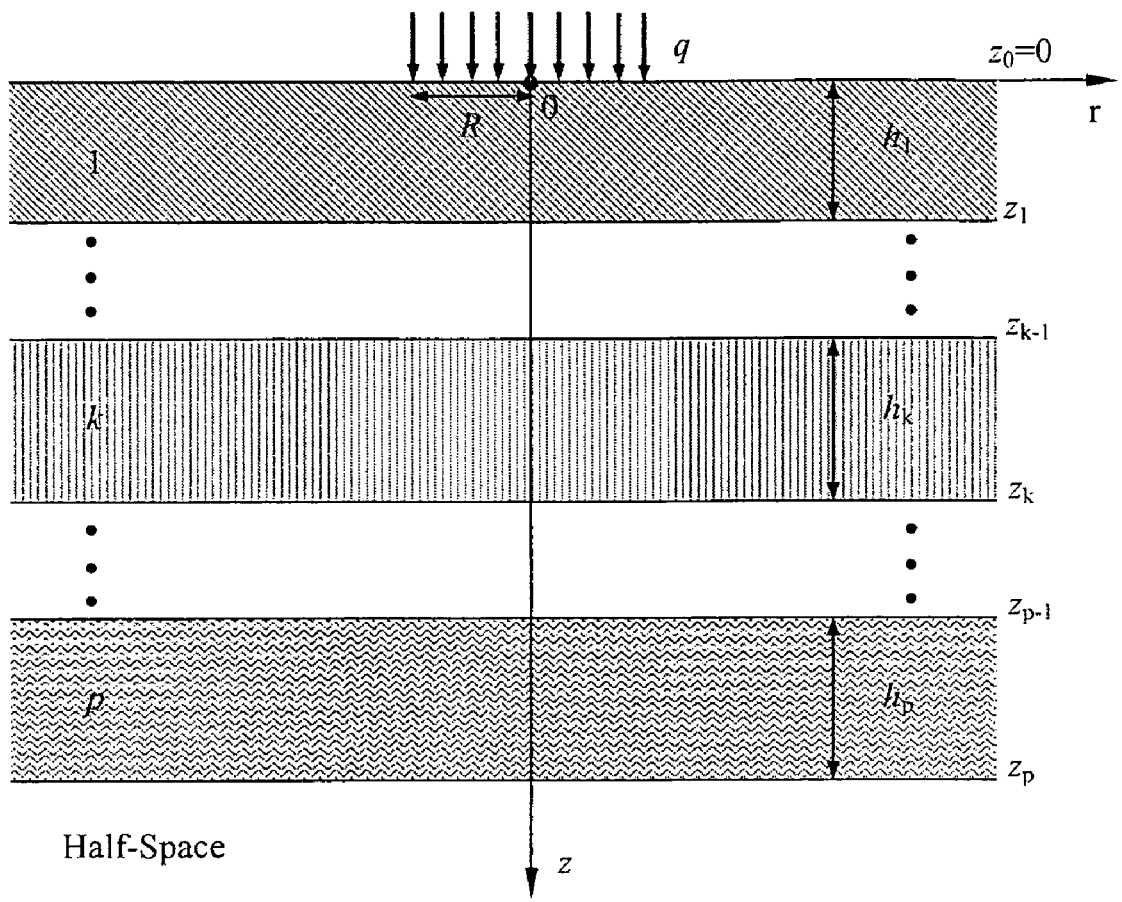
FIG. 1 is a representation of a multilayered elastic half-space under uniform vertical load q within the circle of radius R.

In understanding the present invention, one should consider a layered half space made up of p parallel, elastic isotropic layers lying over an elastic isotropic half space. The layers are numbered serially with the layer at the top being layer 1 and the last layerp, which is just above the half space (see FIG. 1). Initially, place the cylindrical coordinate on the surface with the z-axis pointing into the layered half space. The k-th layer is bounded by the interfaces $z=z_{k-1}$, $z_k$. As such, $z_{k-1}$ is the coordinate of the upper interface of the k-th layer, and $z_k$ that of the lower interface. The thickness of the k-th layer is $h_k=z_k-z_{k-1}$, with $z_0=0$ and $z_p=H$, where H is the depth of the last layer interface. The top surface is subject to uniform unit pressure within a circle of radius R and we want to find the response at different surface stations; this is the primitive problem. For a well-posed problem, the solution in the homogeneous half space of the layered system should be finite when the physical dimension approaches infinity.

While not wishing to be bound by any one particular method of joining interfaces, in some embodiments the interfaces between adjacent layers can be welded, braised, glued, cemented, chemically bonded. Furthermore, some embodiments can include graded transitions from one layer to another. Some embodiments can include any combination of the foregoing methods for joining interfaces.

For the isotropic elastic solid, there are, in each layer, the following governing equations in the cylindrical coordinates:

1) Equilibrium equations without body force:

$$\frac{\partial \sigma_{rr}}{\partial r} + \frac{\partial \sigma_{r\theta}}{r\partial \theta} + \frac{\partial \sigma_{rz}}{\partial z} + \frac{\sigma_{rr}-\sigma_{\theta\theta}}{r} = 0 \quad (1)$$

$$\frac{\partial \sigma_{r\theta}}{\partial r} + \frac{\partial \sigma_{\theta\theta}}{r\partial \theta} + \frac{\partial \sigma_{\theta z}}{\partial z} + \frac{2\sigma_{r\theta}}{r} = 0$$

$$\frac{\partial \sigma_{rz}}{\partial r} + \frac{\partial \sigma_{\theta z}}{r\partial \theta} + \frac{\partial \sigma_{zz}}{\partial z} + \frac{\sigma_{rz}}{r} = 0$$

where $\sigma_{ij}$ is the stress tensor.

2) Constitutive relations:

$$\sigma_{rr} = c_{11}\gamma_{rr} + c_{12}(\gamma_{\theta\theta} + \gamma_{zz}) \quad (2)$$

$$\sigma_{\theta z} = c_{44}\gamma_{\theta z}$$

where $$c_{11} = \frac{E(1-\nu)}{(1+\nu)(1-2\nu)};\ c_{12} = \frac{E\nu}{(1+\nu)(1-2\nu)};\ c_{44} = \frac{E}{2(1+\nu)}. \quad (3)$$

The constitutive relations for the other normal and shear components can be found similarly. While in Eq. (2), $\gamma_{ij}$ are the engineering strain components, in Eq. (3), E and $\nu$ are, respectively, Young's modulus and Poisson's ratio.

3) The strain-displacement relations:

$$\gamma_{rr} = \frac{\partial u_r}{\partial r},\ \gamma_{\theta\theta} = \frac{\partial u_\theta}{r\partial\theta} + \frac{u_r}{r},\ \gamma_{zz} = \frac{\partial u_z}{\partial z} \quad (4)$$

$$\gamma_{\theta z} = \frac{\partial u_\theta}{\partial z} + \frac{\partial u_z}{r\partial\theta},\ \gamma_{rz} = \frac{\partial u_z}{\partial r} + \frac{\partial u_r}{\partial z},\ \gamma_{r\theta} = \frac{u_r}{r\partial\theta} + \frac{\partial u_\theta}{\partial r} - \frac{u_\theta}{r}$$

where $u_i$ is the displacement field.

2. General Solution in Terms of Cylindrical System of Vector Functions

The cylindrical system of vector functions is very convenient in treating axisymmetric problem and it is defined as (Pan, 1989a,b, 1997)

$$L(r, \theta; \lambda, m) = e_z S(r, \theta; \lambda, m), \quad (5)$$

$$M(r, \theta; \lambda, m) = \left(e_r \frac{\partial}{\partial r} + e_\theta \frac{\partial}{r\partial\theta}\right) S(r, \theta; \lambda, m),$$

$$N(r, \theta; \lambda, m) = \left(e_r \frac{\partial}{r\partial\theta} - e_\theta \frac{\partial}{\partial r}\right) S(r, \theta; \lambda, m)$$

with $$S(r, \theta; \lambda, m) = \frac{1}{\sqrt{2\pi}} J_m(\lambda r) e^{im\theta}, \quad (6)$$

where $J_m(\lambda r)$ is the Bessel function of order m, with m=0 corresponding to the axisymmetric deformation, which will be discussed in detail herein. It should be also noticed that the scalar function S in Eq. (6) satisfies the Helmholtz equation $$\frac{\partial^2 S}{\partial r^2} + \frac{\partial S}{r\partial r} + \frac{\partial^2 S}{r^2 \partial\theta^2} + \lambda^2 S = 0. \quad (7)$$

The cylindrical system of vector functions is an extension of the Hankel transform and can be directly applied to a vector function. Since this vector function system (Eq. (5)) forms an orthogonal and complete space, any integrable vector and/or scalar function can be expressed in terms of it. In particular, the displacement and traction (with the z-axis as the normal) vectors can be expressed as $$u(r, \theta, z) = \sum_m \int_0^{+\infty} \begin{bmatrix} U_L(z)L(r, \theta) + \\ U_M(z)M(r, \theta) + U_N(z)N(r, \theta) \end{bmatrix} \lambda d\lambda \quad (8)$$

$$t(r, \theta, z) \equiv \sigma_{rz} e_r + \sigma_{\theta z} e_\theta + \sigma_{zz} e_z \quad (9)$$

$$= \sum_m \int_0^{+\infty} \begin{bmatrix} T_L(z)L(r, \theta) + \\ T_M(z)M(r, \theta) + T_N(z)N(r, \theta) \end{bmatrix} \lambda d\lambda.$$

Making use of these expansions along with the strain-displacement and constitutive relations, we have, in general, $$u_r(r, \theta, z) = \sum_m \int_0^\infty \left(U_M \frac{\partial S}{\partial r} + U_N \frac{\partial S}{r\partial\theta}\right)\lambda d\lambda \quad (10a)$$

$$u_\theta(r, \theta, z) = \sum_m \int_0^\infty \left(U_M \frac{\partial S}{r\partial\theta} - U_N \frac{\partial S}{\partial r}\right)\lambda d\lambda \quad (10b)$$

$$u_z(r, \theta, z) = \sum_m \int_0^\infty U_L S \lambda d\lambda \quad (10c)$$

$$\sigma_{rr}(r, \theta, z) = \sum_m \int_0^\infty \left[c_{11}\left(U_M \frac{\partial^2 S}{\partial r^2} + U_N \frac{\partial^2 S}{r\partial r \partial\theta} - U_N \frac{\partial S}{r^2 \partial\theta}\right) + \right. \quad (11a)$$

$$c_{12}\left(U_M \frac{\partial^2 S}{r^2 \partial\theta^2} + U_M \frac{\partial S}{r\partial r} - U_N \frac{\partial^2 S}{r\partial r \partial\theta} + U_N \frac{\partial S}{r^2 \partial\theta}\right) +$$

$$\left. c_{12} \frac{dU_L}{dz} S \right]\lambda d\lambda$$

-continued $$\sigma_{\theta\theta}(r, \theta, z) = \sum_m \int_0^\infty \left[ c_{12}\left(U_M \frac{\partial^2 S}{\partial r^2} + U_N \frac{\partial^2 S}{r\partial r\partial\theta} - U_N \frac{\partial S}{r^2\partial\theta}\right) + \right.$$
$$\left. c_{11}\left(U_M \frac{\partial^2 S}{r^2\partial\theta^2} + U_M \frac{\partial S}{r\partial r} - U_N \frac{\partial^2 S}{r\partial r\partial\theta} + U_N \frac{\partial S}{r^2\partial\theta}\right) + c_{12}\frac{dU_L}{dz}S \right] \lambda d\lambda \quad (11b)$$

$$\sigma_{zz}(r, \theta, z) = \sum_m \int_0^\infty \left[ -\lambda^2 c_{12} U_M + c_{11}\frac{dU_L}{dz} \right] S\lambda d\lambda \quad (11c)$$

$$\sigma_{\theta z}(r, \theta, z) = c_{44} \sum_m \int_0^\infty \left( \frac{dU_M}{dz}\frac{\partial S}{r\partial\theta} - \frac{dU_N}{dz}\frac{\partial S}{\partial r} + \frac{1}{r}U_L\frac{\partial S}{\partial\theta} \right) \lambda d\lambda \quad (11d)$$

$$\sigma_{rz}(r, \theta, z) = c_{44} \sum_m \int_0^\infty \left( \frac{dU_M}{dz}\frac{\partial S}{\partial r} + \frac{dU_N}{dz}\frac{\partial S}{r\partial\theta} + U_L\frac{\partial S}{\partial r} \right) \lambda d\lambda \quad (11e)$$

$$\sigma_{r\theta}(r, \theta, z) = c_{44} \sum_m \int_0^\infty \left[ \begin{array}{c} U_M\left(\frac{2\partial^2 S}{r\partial r\partial\theta} - \frac{2\partial S}{r^2\partial\theta}\right) + \\ U_N\left(\frac{\partial^2 S}{r^2\partial\theta^2} - \frac{\partial^2 S}{\partial r^2} + \frac{\partial S}{r\partial r}\right) \end{array} \right] \lambda d\lambda. \quad (11f)$$

The relation of the expansion coefficients between $T_I$ and $U_I$ (I=L, M, N) can be found by comparing Eqs. (9) to (11c, d, e)

$$T_L = -\lambda^2 c_{12} U_M + c_{11}\frac{dU_L}{dz}, \quad (12a,b,c)$$
$$T_M = c_{44}\left(U_L + \frac{dU_M}{dz}\right),$$
$$T_N = c_{44}\frac{dU_N}{dz}.$$

Substituting the stress expansion (11) into the equilibrium equation (1), one finds $$\frac{dT_L}{dz} - \lambda^2 T_M = 0, \quad (13a,b,c)$$
$$-\lambda^2 c_{11} U_M + c_{12}\frac{dU_L}{dz} + \frac{dT_M}{dz} = 0,$$
$$\frac{dT_N}{dz} - \lambda^2 c_{44} U_N.$$

Noticing that the N-type solution is independent to the L&M-type solution, the following two sets of coefficient vectors are introduced $$[E] = [U_L, \lambda U_M, T_L/\lambda, T_M]^t \quad (14a)$$
$$[E^N(z)] = [U_N(z), T_N(z)/\lambda]^t \quad (14b)$$

then the homogeneous solution in each layer from Eqs. (12) and (13) are found to be $$[E(z)] = [Z(z)][K] \quad (15a)$$
$$[E^N] = [Z^N(z)][K^N] \quad (15b)$$

where $[K]$ and $[K^N]$ are column coefficient vectors of $4 \times 1$ and $2 \times 1$, respectively, with their elements to be determined by the interface and/or boundary conditions. The matrices $[Z(z)]$ and $[Z^N(z)]$ are the solution matrices given in Pan (1989a,b).

The propagating relations for the coefficient vectors $[E]$ and $[E^N]$ of k-th layer at the z-level $z_{k-1}$ and that at $z_k$, are found to be $$[E(z_{k-1})] = [a_k][E(z_k)], \quad (16a)$$
$$[E^N(z_{k-1})] = [a_k^N][E^N(z_k)] \quad (16b)$$

where $[a_k]$ and $[a_k^N]$ are the propagator matrices for the k-th layer, with their elements given in Pan (1989a,b).

3. Solution for the Unit Circular Load

Assume that a uniform vertical surface load (i.e. pressure or normal stress) of magnitude q is applied within the circle of r=R (FIG. 1), then the traction boundary condition on the surface z=0 is expressed as:

$$\sigma_{zz} = \begin{cases} -q & r < R \\ 0 & r > R \end{cases} \quad (17)$$
$$\sigma_{rz} = \sigma_{\theta z} = 0 \quad 0 \leq r \leq \infty.$$

Therefore, the corresponding expansion coefficients in the cylindrical systems of vector functions are:

$$T_L(\lambda, 0) = -\frac{qR\sqrt{2\pi}}{\lambda} J_1(\lambda R) \quad (18)$$
$$T_M(\lambda, 0) = T_N(\lambda, 0) = 0.$$

The solution to the N-type problem is identically zero and therefore we need to solve the L&M-type problem (axisymmetric) only. First solve the problem in the transformed domain (i.e., in terms of the expansion coefficients). Propagating the propagator matrix $[a_k]$ from the top of the homogeneous half space z=H to the surface z=0, we find $$[E(0)] = [G][K_p], \quad (19)$$

where $$[G] = [a_1][a_2]\cdots[a_p][Z_p(H)], \quad (20).$$

The unknown coefficients $[K_p]$ are those in the half-space. As the solution in the half space should be bounded, the first and third elements in $[K_p]$ should be zero (Pan, 1997). The remaining two unknown coefficients can be determined by the two boundary conditions on the surface z=0 as given by Eq. (18) (for the L- and M-components only).

After the unknown coefficients in $[K_p]$ are determined, the expansion coefficients at any depth (e.g. in the k-th layer with $z_{k-1} \leq z \leq z_k$) can be obtained exactly as:

$$[E(z)] = [a_k(z - z_{k-1})][a_{k+1}]\cdots[a_p][Z_p(H)][K_p]. \quad (21).$$

In general, direct multiplication of the propagator matrix $[a_k]$ can be carried out in order to propagate the transformed domain solution from one layer to the next. However, as discussed in Pan (1997), Yue & Yin (1998), and more recently by Fukahata & Matsu'ura (2005), overflow can occur from multiplication of matrices in equations (20) and (21). Fortunately, this can be overcome by factoring out the exponentially growing factor in the elements of the propagator matrix. The resulting modified propagator matrices have no element growing exponentially, and therefore there will be no overflow problem for a multilayered half space having any number of layers (no matter what is the thickness of each layer).

After solving the problem in the transformed domain, the displacement and stress solutions at any location in the physical domain can be expressed (independent of θ because of symmetry) as:

$$u_r(r, z) = -\frac{1}{\sqrt{2\pi}} \int_0^\infty (\lambda U_M) J_1(\lambda r) \lambda \, d\lambda \quad (22a)$$

$$u_\theta(r, z) = 0 \quad (22b)$$

$$u_z(r, z) = \frac{1}{\sqrt{2\pi}} \int_0^\infty (U_L) J_0(\lambda r) \lambda \, d\lambda \quad (22c)$$

$$\sigma_{rz}(r, z) = -\frac{1}{\sqrt{2\pi}} \int_0^\infty (T_M) J_1(\lambda r) \lambda^2 \, d\lambda \quad (23a)$$

$$\sigma_{\theta z}(r, z) = \sigma_{r\theta}(r, z) = 0 \quad (23b)$$

$$\sigma_{zz}(r, z) = \frac{1}{\sqrt{2\pi}} \int_0^\infty \left(\frac{T_L}{\lambda}\right) J_0(\lambda r) \lambda^2 \, d\lambda \quad (23c)$$

$$\sigma_{rr}(r, z) = \quad (23d)$$
$$\frac{v}{1-v}\sigma_{zz} + \frac{2c_{44}}{\sqrt{2\pi}}\int_0^\infty (\lambda U_M)\left[-\frac{1}{1-v}J_0(\lambda r)\lambda + \frac{J_1(\lambda r)}{r}\right]\lambda \, d\lambda$$

$$\sigma_{\theta\theta}(r, z) = \frac{2v}{1-v}\sigma_{zz} - \sigma_{rr} - \frac{1}{\sqrt{2\pi}} \frac{E}{(1-v)}\int_0^\infty (\lambda U_M) J_0(\lambda r) \lambda^2 \, d\lambda \quad (23e)$$

where the expansion coefficients are functions of z and the transform variable $\lambda$.

Of particular interest is the displacement field on the surface, which, in geophysical context is often directly observable using GPS (Bevis et al., 2004) or InSAR. For a uniform circular load, the horizontal (radial) and vertical displacements on the surface can be expressed as:

$$u_r(r, 0) = qR \int_0^\infty \frac{D_1}{\lambda} J_1(\lambda R) J_1(\lambda r) \, d\lambda \quad (24a)$$

$$u_z(r, 0) = -qR \int_0^\infty \frac{D_0}{\lambda} J_1(\lambda R) J_0(\lambda r) \, d\lambda \quad (24b)$$

where $$D_0 = \frac{G_{12}G_{44} - G_{14}G_{42}}{G_{32}G_{44} - G_{34}G_{42}}; \quad D_1 = \frac{G_{22}G_{44} - G_{24}G_{42}}{G_{32}G_{44} - G_{34}G_{42}} \quad (24c)$$

with $G_{ij}$ being the elements of the matrix [G] in Eq. (20). This matrix is a function of the transform variable $\lambda$, the elastic properties of the layered half-space, and the thickness of each layer.

To find the physical domain solutions, the transformed-domain results need to be integrated numerically. It is further noted that the integrands in the infinite integrals for the displacements involve products of Bessel functions that are oscillatory and go to zero slowly as their argument approaches infinity. Thus, the common numerical integration methods, such as the trapezoidal rule or Simpson's rule, are not suitable. While numerical integration of infinite integrals involving a single Bessel function has been discussed by Chave (1983) and Lucas and Stone (1995), the corresponding numerical integration involving products of Bessel functions of different orders has been studied by Lucas (1995) using adaptive Gaussian quadrature. The present invention adopts and includes adaptive Gaussian quadrature due to its accuracy and efficiency.

Based on this method, the infinite integral is expressed as a summation of:

$$\int_0^{+\infty} f(\lambda) J_m(\lambda R) J_n(\lambda r) \, d\lambda = \quad (25)$$
$$\int_0^{r_{max}} f(\lambda) J_m(\lambda R) J_n(\lambda r) \, d\lambda + \int_{r_{max}}^{+\infty} f(\lambda) J_m(\lambda R) J_n(\lambda r) \, d\lambda.$$

The finite and infinite integrations on the right-hand side of (25) are then calculated using adaptive Gaussian quadrature (i.e., Rice, 1983; Chave, 1983). Furthermore, in applying Gaussian quadrature, the mW transform and $\epsilon$-algorithm are also introduced for handling the oscillation feature of the integrands and for accelerating the calculation (Lucas, 1995; Lucas and Stone, 1995). In the numerical analysis presented below, the relative and absolute errors have been set, at $10^{-4}$ and $10^{-5}$ respectively.

4. SEMI Method for Surface Displacement Fields

As can be observed from Eq. (24), for different surface locations (i.e. stations) on a substrate, the surface displacements need to be calculated one by one, which would involve substantial computation if direct methods were used. The SEMI approach involves using the computationally expensive direct method to compute a very accurate result at a limited number of reference points, or knots, and to estimate the two components of displacement at intermediate distances by interpolation. There are many appropriate interpolation schemes, and the present invention is not limited to any particular scheme. A suitable exemplary scheme is detailed below. Thus the method of the present invention can include any of a variety of interpolation methods.

Figure 2:
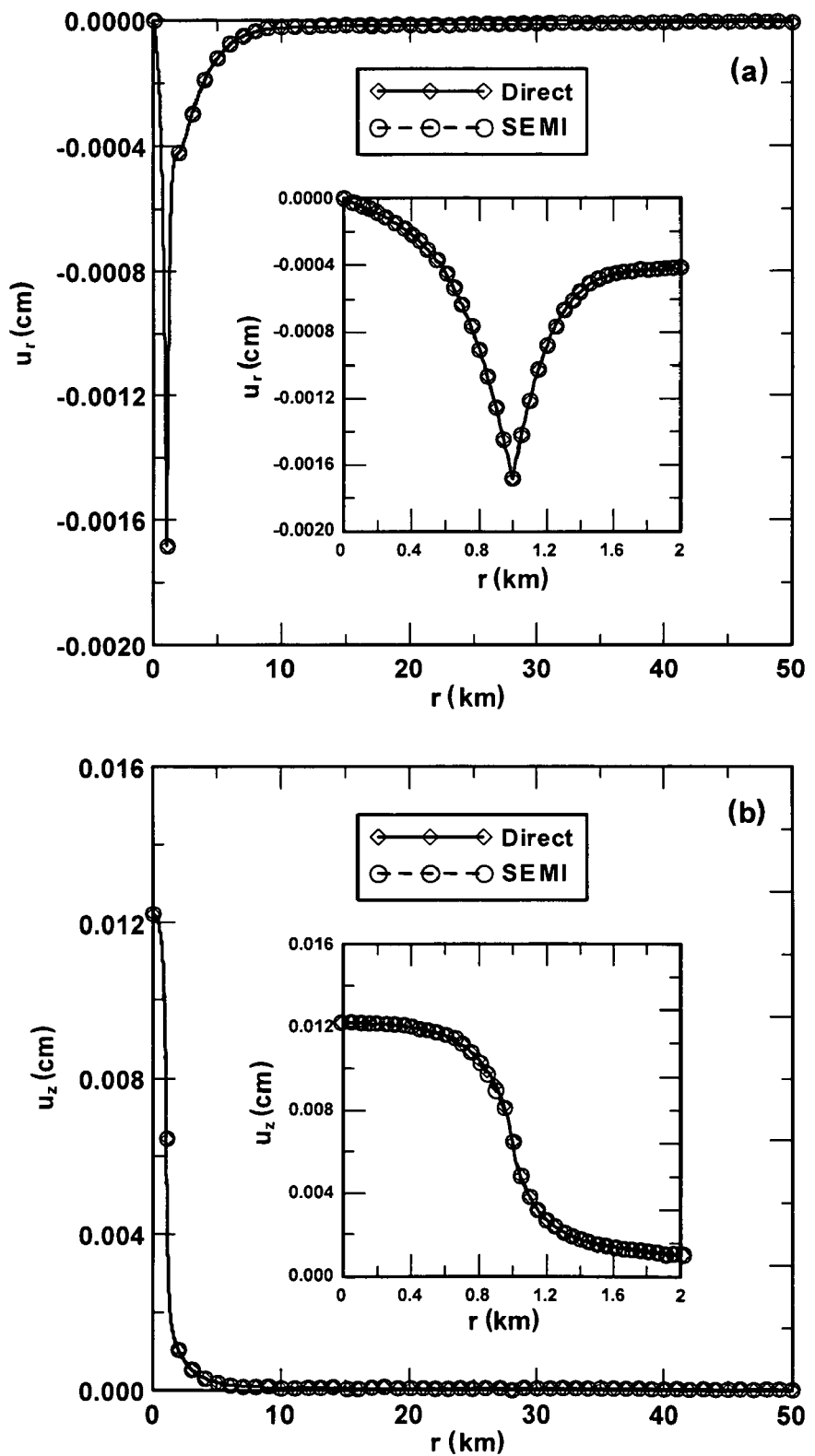
FIG. 2 is a graph showing a comparison of the surface radial ($u_r$ in (a)) and vertical ($u_z$ in (b)) displacements for layered Model 1: Direct vs. SEMI (based on Case II with 31 pre-calculation points)

Based on the feature of the surface displacement components as functions of r (as shown in FIGS. 2a,b and 3a,b for the two typical layered models given in Tables 1 and 2; many other layered models have been tested with all of them showing features similar to those seen in FIGS. 2 and 3), our example implementation of the SEMI method divides the surface into three different sections: A near-field (from 0 to 2R), a middle-field (2R to 40R), and a far-field (40R to, say, 100R) section. As can be observed from both FIGS. 2 and 3, in the near-field the displacement reaches the largest magnitude with the most severe changes in its slope and high-order derivatives occurring at the boundary of the circle. In the middle field, the variation of the displacement is very smooth and gentle. Finally in the far-field, the displacement asymptotically approaches zero. Therefore, in these different sections one should use different interpolation schemes. After many testing runs, we decided to employ the B-spline in physical domain for the near field, B-spline in natural logarithmic ln-domain for the middle field, and the inverse (1/r) B-spline for the far-field. These are discussed separately below.

1). Near- and Middle-Field Pre-Calculation with B-Spline

Splines are piecewise polynomials of degree n joined together at control points with n−1 continuous derivatives. These control or break points of splines are often called knots. If $n \geq 2$, then the spline is smooth. In the B-spline algorithm, the targeted function, i.e. u(r), is expressed as (de Boor, 1979; Rice, 1983)

$$u(r) = \sum_{j=1}^{N} a_j B_j(r) \quad (26)$$

where $B_j=B_{j,k,t}$ denotes the j-th B-spline of order k with respect to the knot sequence t, and the coefficients $a_j$ are solved from the following equation using the function values at data points $r_i$ (i.e., requires that the B-spline passes exactly through each control point)

$$\sum_{j=1}^{N} a_j B_j(r_i) = u(r_i). \tag{27}$$

In B-spline, different orders using the knot sequence based upon the r-values of the data, i.e. from order 2 (quadratic) through order 8, can be selected. In the method of the present invention, the order is fixed at 3, and a different number of control points are chosen to approximate both the near- and middle-fields.

Due to varying character of the surface displacement in the near- and middle-fields, different spline-based interpolation methods are developed in each sector. In the near field from 0 to 2R, there is a well-known singular point in the surface stress on the edge of the circle r=R. Such a singularity corresponds to the sharp slope (and second order derivative) changes in displacements which cannot be easily treated even with the B-spline approximation. Therefore, the near field is further separated into three subsections: 0 to R−δ, R−δ to R+δ, and R+δ, to 2R. While the direct physical-domain B-spline is utilized to approximate the displacements in the first and third subsections, direct calculation with linear interpolation is proposed for the middle subsections. In some embodiments δ can be about 0.03R. In other embodiments δ can take on values between about 0.02R and 0.04R, 0.04R and 0.06R, 0.06R and 0.08R, or even 0.08R and 0.10R. Here, as elsewhere in the specification and claims, ranges may be varied. Furthermore, in the first and third B-spline domains a graded distance g is used to find the selected point locations. For these two subsections, the graded distance g can be about 1.5 with increasing $r_i$, which means $|r_{i+1}-r_i|=1.5|r_i-r_{i-1}|$. In other embodiments g can be from about 1 to 2.

Figure 4:
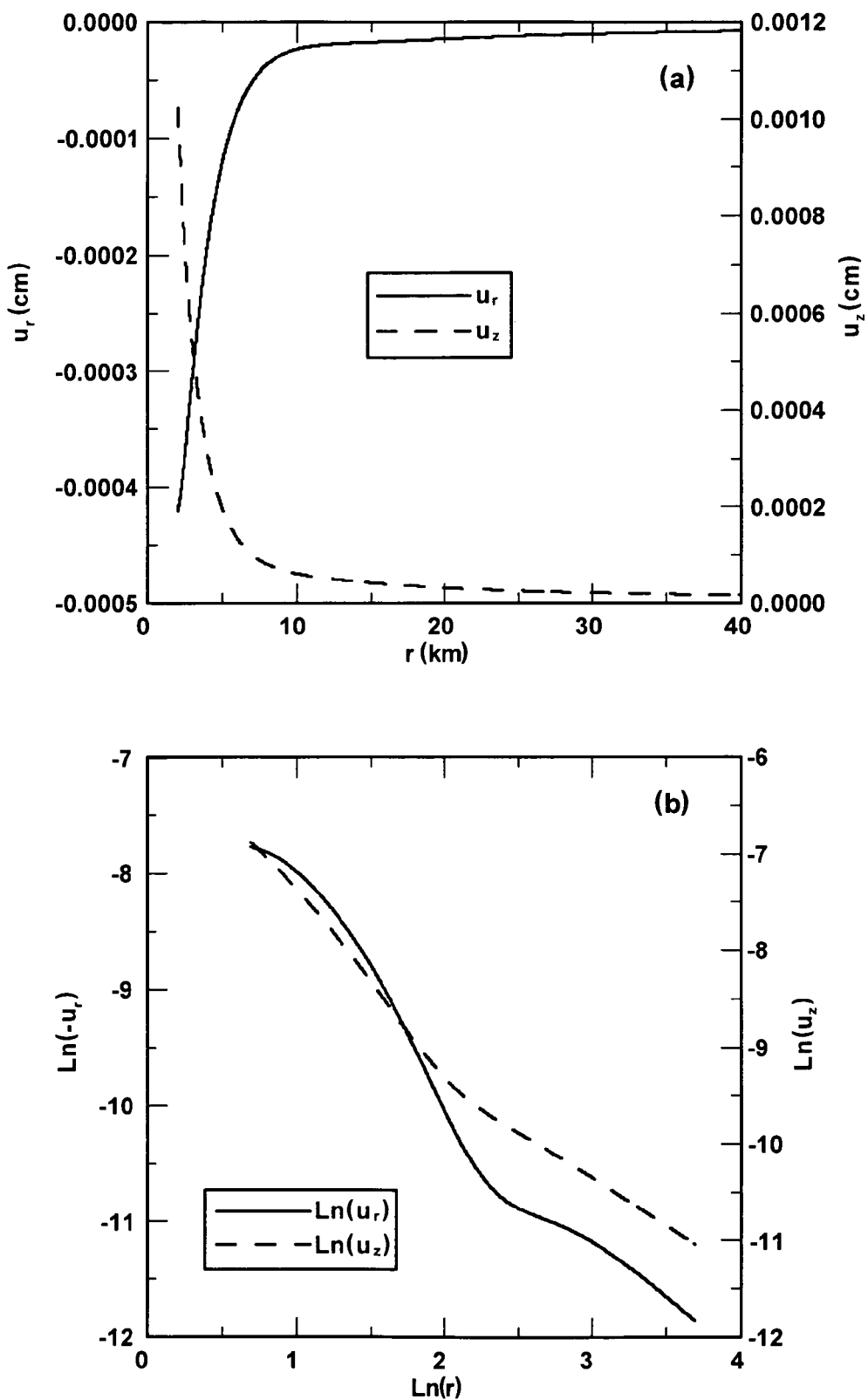
FIG. 4 is a graph showing the variation of the surface radial and vertical displacements vs. radial distance r for layered Model 1: In the physical domain (a) and in the nature ln domain (b)

According to some embodiments the B-spline is also applied to the middle field, i.e. from about 2R to 40R. However, instead of using the B-spline in the physical domain directly, we use it in the natural logarithmic domain. The B-spline interpolation scheme of the present invention is based on the fact that the displacement response in the nature ln-domain is smoother than that in the physical domain. This can be observed in FIGS. 4a-b for the horizontal and vertical displacement distributions for Model 1 in the physical—(FIG. 4a) and natural ln—(FIG. 4b) domains. Numerical experiments based on different layered half-space structures further suggest that it is convenient to work in the natural ln-domain. Furthermore, due to the smooth feature of the displacement in the natural ln-domain, the control points are uniformly distributed in the ln-domain (ln(r)). This is in contrast to the near field where a graded distance is chosen with increasing r in the physical domain.

2). Far-Field Pre-Calculation using Inverse B-spline

For r larger than 40R, the displacement field decays to zero, inversely proportional to the distance. Therefore, for a given circular load, the magnitude of the displacements in the far-field would be small or very small as compared to those in the near- and middle-fields. However, the present invention still includes this far-field response from r=40R all the way, say to r=100R (if required, further extension to r=1000R or even r=5,000R can be easily achieved by just adding a couple of more control points as for the r=100R case discussed below).

In this section, the present invention includes the following B-spline in terms of the inverse distance x=1/r for the displacement u ($u_r$ and $u_z$) as $$u(x) = \sum_{j=1}^{N} b_j B_j(x) \tag{28}$$

where the coefficients $b_j$ are solved by using the function values at the predetermined control points $x_i$ ($x_i=1/r_i$) in the interval of r=40R–100R, similar to (27). In a couple of special cases where the far-field displacement decays monotonically, a simple asymptotical expansion may give somewhat more accurate results than the inverse B-spline. Thus, the present invention alternatively includes such asymptotic expansions. But, the inverse B-spline set forth herein can be applied generally.

5. Direct vs. SEMI Methods: Numerical Comparison

In this section, two typical layered models listed in Tables 1 and 2 are selected to illustrate the SEMI method. While Model 1 corresponds to the earth structure, Model 2 is the inverse layup of the Model 1 material properties, which is a typical layered pavement structure. Furthermore, for each model, four different cases with different number of selected control points (Case I with 20 points, Case II with 31 points, Case III with 54 points, and Case IV with 99 points) are evaluated (Table 3).

Figure 3:
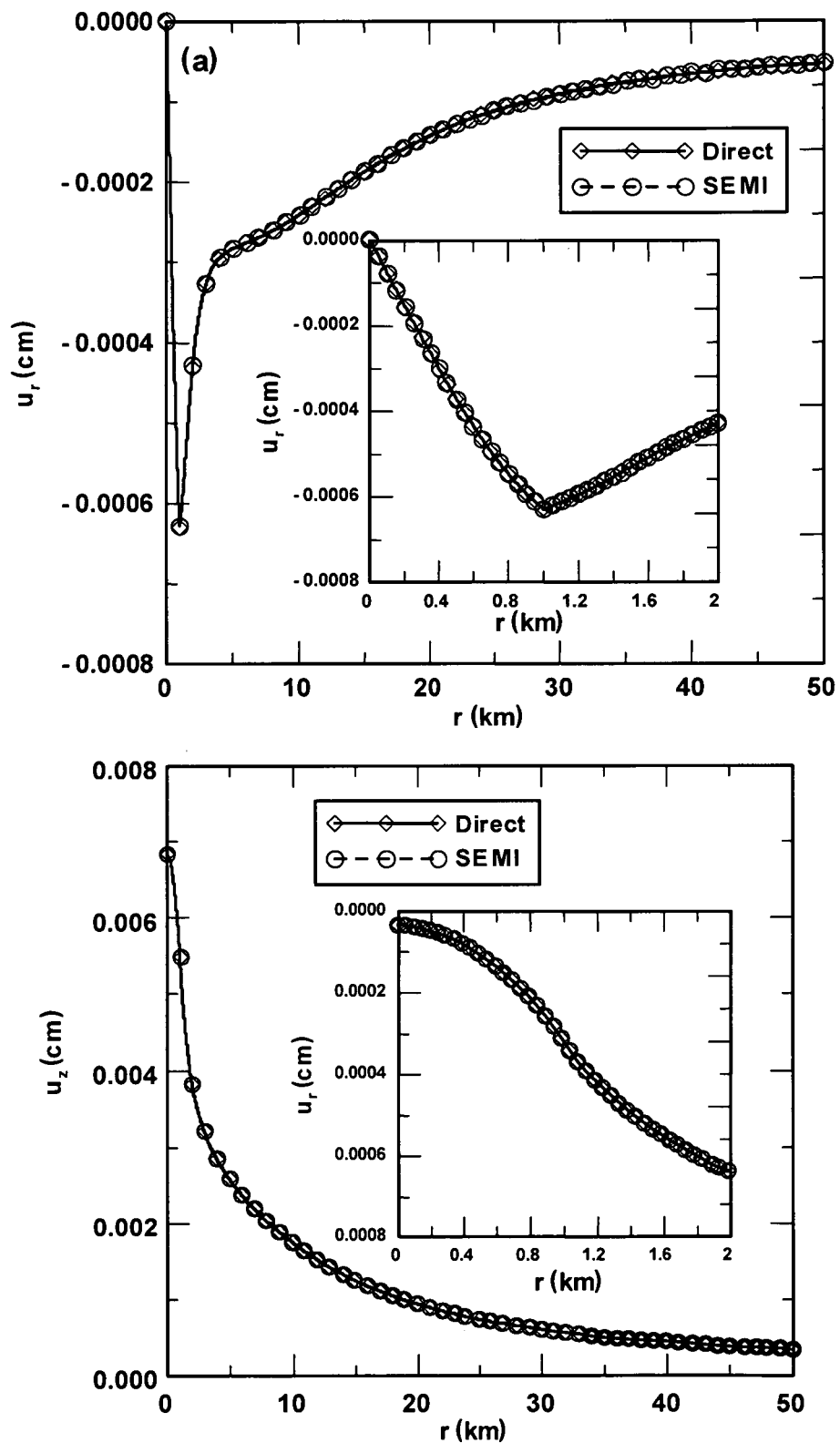
FIG. 3 is a graph of a comparison of the surface radial ($u_r$ in (a)) and vertical ($u_z$ in (b)) displacements for layered Model 2: Direct vs. SEMI (based on Case II with 31 pre-calculation points)

First, shown in FIGS. 2 and 3 are the comparison of the surface displacements based on both the direct and SEMI methods for both models 1 and 2 with 31 pre-calculation points for SEMI (i.e., Case II), with station points varying from 0 to 50R at an increment of 0.1R. The inserted figures are the zoom-in results from 0 to 2R to show the rapid variation of the displacement fields in the near field. As can be observed from these figures, the SEMI results agree well with those calculated directly.

Figure 5:
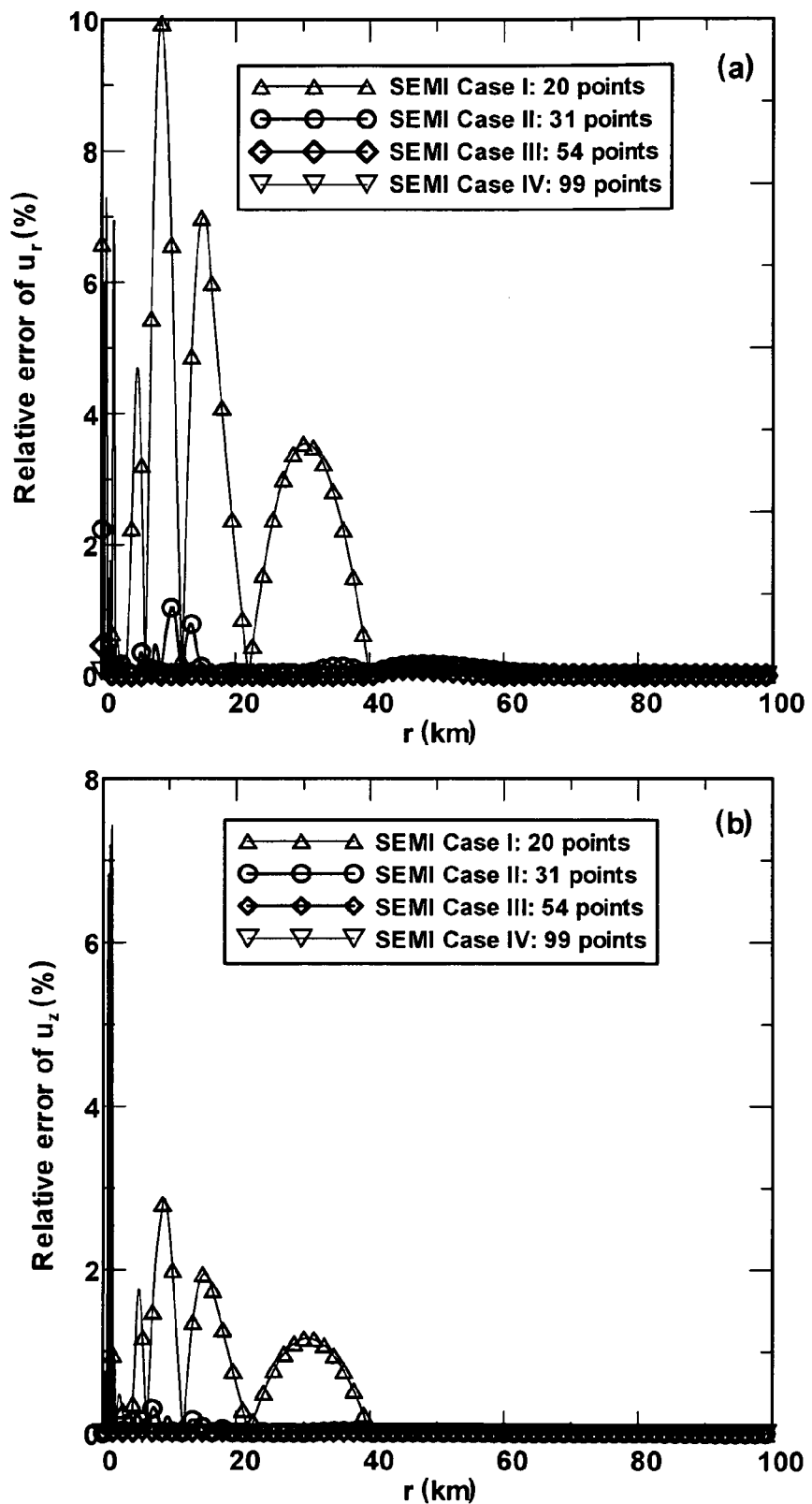
FIG. 5 is a graph of the relative errors in surface displacements $u_r$ (a) and $u_z$ (b) for Model 1 for the four SEMI Cases with different number of pre-calculation points.
Figure 6:
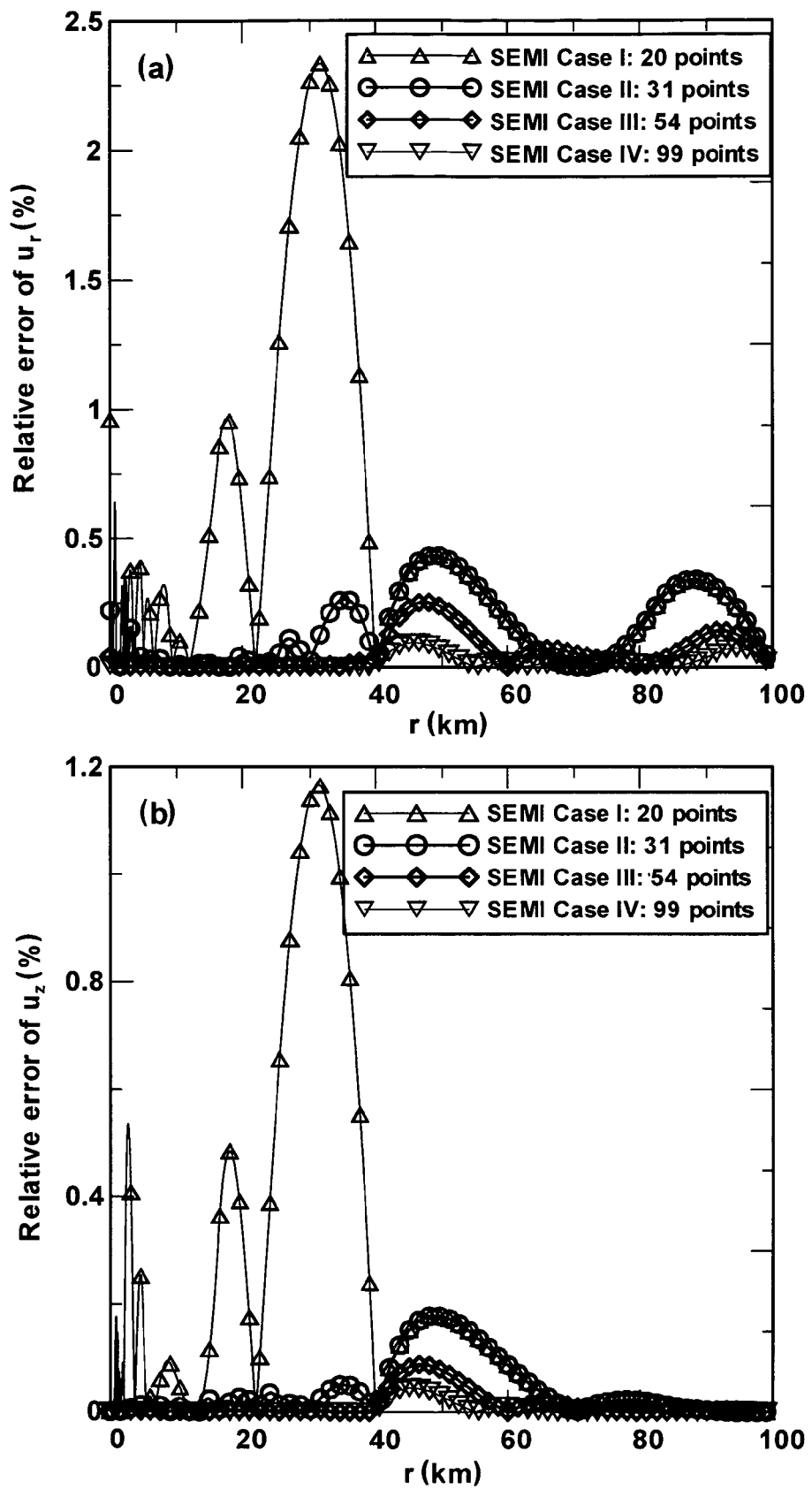
FIG. 6 is a graph of the relative errors in surface displacements $u_r$ (a) and $u_z$ (b) for Model 2 for the four SEMI Cases with different number of pre-calculation points.

Second, to quantitatively demonstrate the accuracy of the SEMI method, we have also estimated the relative errors (FIGS. 5 and 6) and the RMS relative errors (Table 3) between the direct and SEMI approaches. Listed in Table 3 are the SEMI results as compared to the direct calculation for Model 1 from r=0 to r=100R for the four Cases I to IV in terms of the RMS relative errors. In this table, "Sect" stands for the three different sections (1 for near-field, 2 for middle-field, and 3 for far-field); "Max" stands for the total number of control points (pts in the table) used in the SEMI approach; $RMS_{ur}$ and $RMS_{uz}$ are the RMS relative errors in the radial and vertical displacements as compared to the direct results, with the maximum between these two being $RMS_{max}$. For these four sets of control points (corresponding to Cases I to IV), we have further plotted the detailed relative errors between the SEMI and the direct methods as the function of r, as presented in FIGS. 5a-b for the radial and vertical displacements for Model 1 and in FIGS. 6a-b for Model 2. FIGS. 5 and 6 show clearly that as the number of control points increases the relative errors in the SEMI solutions decline rapidly.

Figure 7:
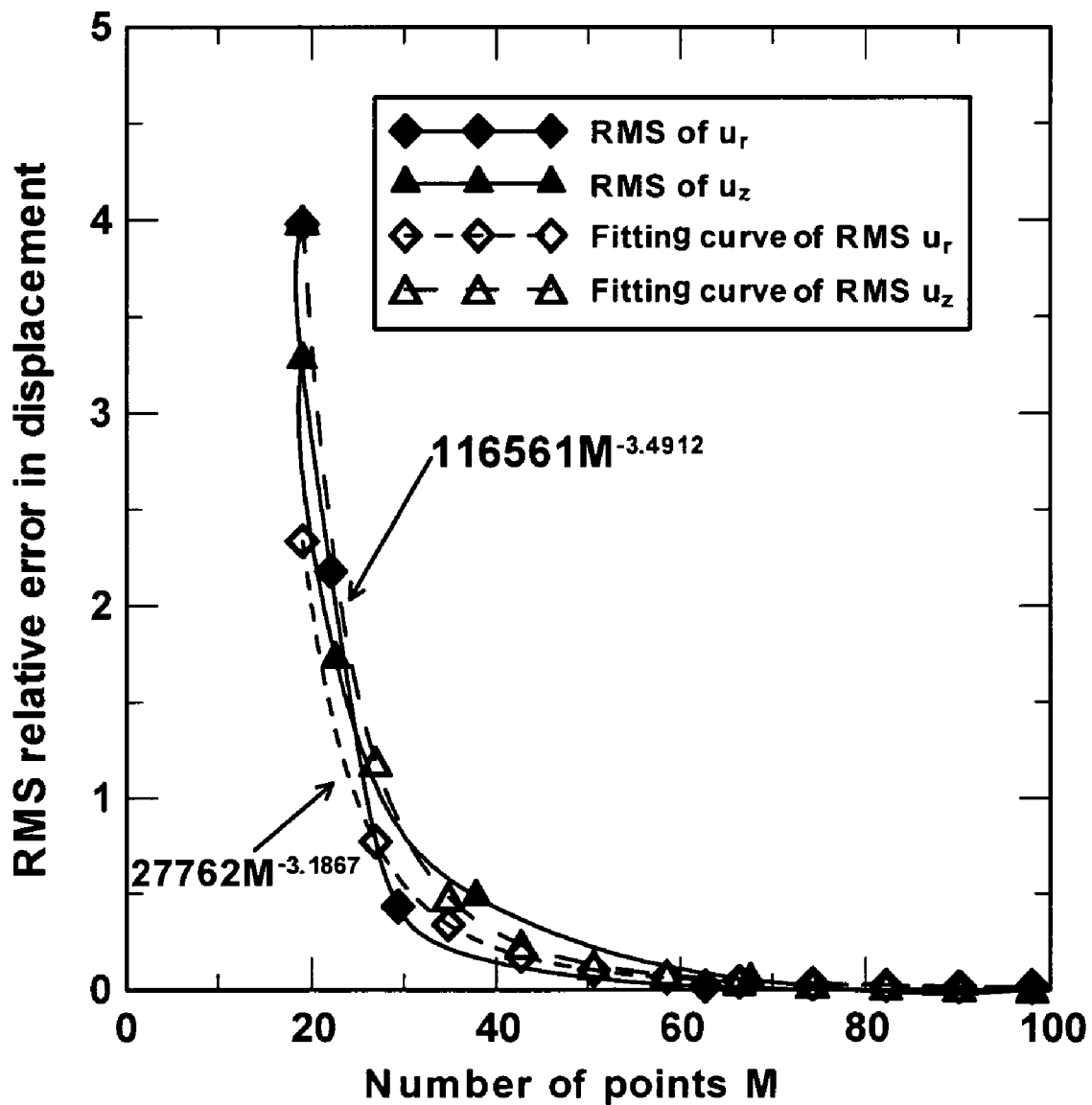
FIG. 7 is a graph of the RMS relative errors of surface displacements $u_r$ and $u_z$ vs. number of pre-calculation points for Model 1.

Third, we have also evaluated the decay behavior of the RMS relative error in displacements as a function of the number M of control points. The RMS relative error is determined by comparing the approximate solutions obtained using the SEMI method with those obtained (far more slowly) via direct evaluation (i.e. the same approach used to compute the displacements at the M control points). The rapid decay trend can be observed in Table 3 for the maximum RMS relative errors and can even be expressed approximately in proportion to $1M^n$, with n being larger than 3 for the whole domain from 0 to 100R. Such a fast decay feature is also shown in FIG. 7 where the RMS relative errors in the displacements $u_r$ and $u_z$ for Model 1 as a function of the total number M, along with their corresponding fitting curves are plotted. The fitted curves for the RMS relative $u_r$ and $u_z$, are, respectively, $27762/M^{3.1867}$ and $116561/M^{3.4912}$.

Finally, for fixed RMS relative errors (i.e., Cases I to IV), we have compared the CPU times based on both the direct and SEMI methods. Listed in Table 4 are the CPU times for the two layered models for four values of M. As can be observed, our SEMI is much faster than the direct method, in particular when the station number is very large. More specifically, for 500 surface stations, the present invention's SEMI method is about 25 times faster than the direct method, and for 100,000 points, the method of the present invention is at least 1,200 times faster than the direct method (when M is 54). Furthermore, there is virtually no difference in CPU time based on the SEMI method when the number of the control points increases from 20 (Case I corresponding to $RMS_{max} \leq 4\%$) to 54 (Case III corresponding to $RMS_{max} \leq 0.2\%$). Even for Case IV which corresponds to the more accurate result (i.e., $RMS_{max} \leq 0.03\%$) with M=99, our SEMI is still about 700 times faster than the direct method.

As can be seen, the present invention is a rapid numerical method for the calculation of surface displacement fields due to a uniform circular loading on the surface of the layered Cartesian half-space. High accuracy solutions can be obtained by combining a cylindrical system of vector functions with the propagator matrix method. Instead of evaluating these solutions at every station of interest, which would be computationally expensive due to the presence of slowly converging integrals, we perform these calculations only at a limited number of control points, and then estimate the displacements at intervening points via interpolation. By varying the number of control points used, one can trade off computational speed and numerical accuracy according to the needs of the application. The SEMI method therefore provides a practical method for calculating the surface response due to any spatial distribution of surface loading by approximating the laterally varying load using a large number of circular loading elements.

There are many alternative ways in which the second (interpolation) stage of the SEMI method can be practiced. The present invention encompasses all of these methods even though only the B-spline is set forth herein. The surface, i.e. the r-axis, is divided into three sections (near-, middle-, and far-fields) with certain number of pre-selected control points in each section. Due to the different character of the displacement function in these sections, three different methods have been developed for interpolating between the control points. For a half-space composed of two-layers over a uniform half-space, computing the loading response at 100,000 different surface locations is achieved more than 1,200 time faster using the SEMI method rather than the direct method, and the RMS relative error in displacement is everywhere less than 0.2%. For maximum RMS relative error less than 0.03%, our SEMI approach is still about 700 times faster than the direct method.

6. General Surface Loading

Figure 8:
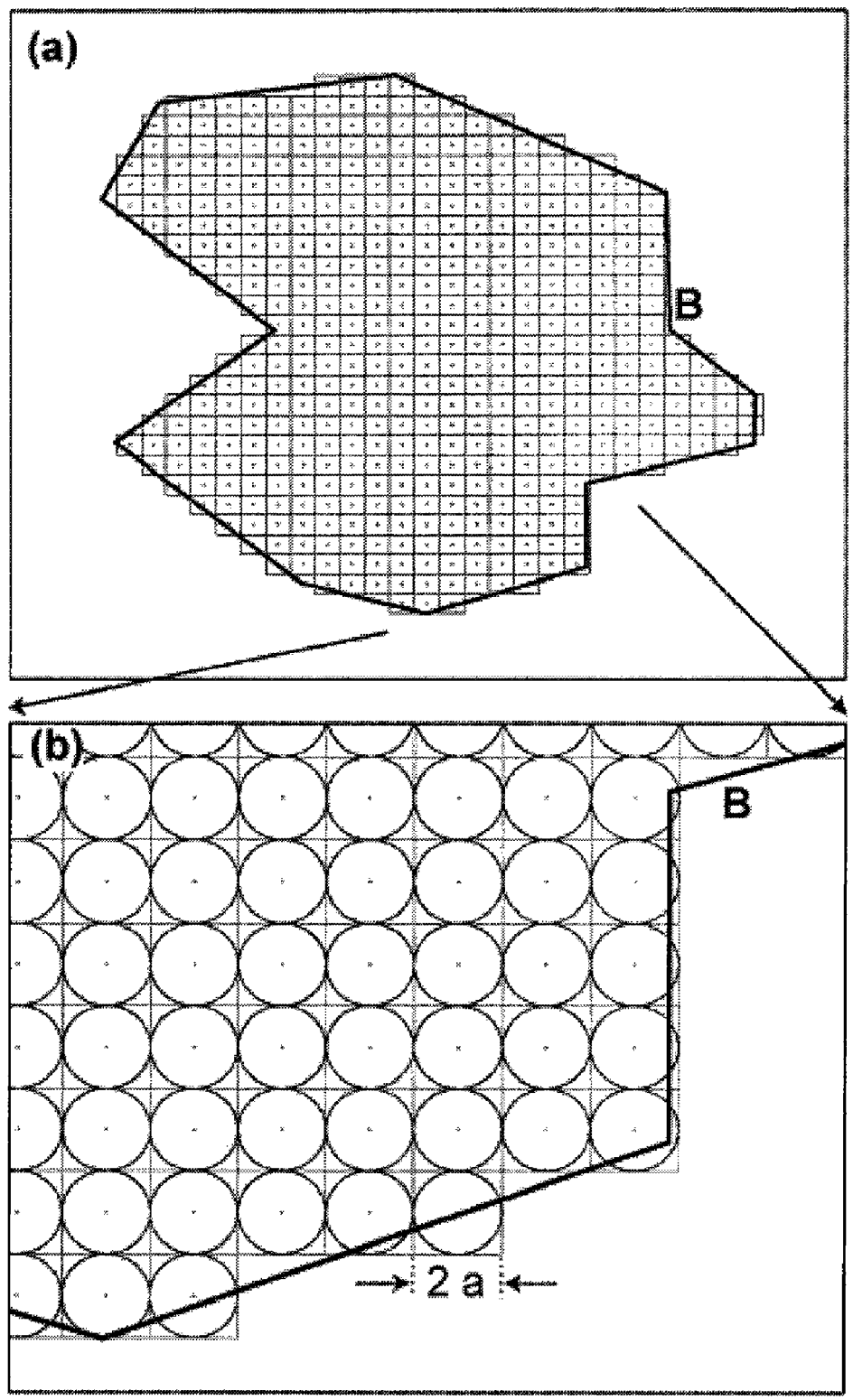
FIG. 8 is a representation of an arbitrary loading area on the surface of the layered half space and its approximation by circular loading elements.

Once the primitive problem is solved using the SEMI method as presented above, the surface response at any station due to the arbitrary loading of the layered half space can then be easily obtained by approximating the arbitrary loading area on the surface with many circular loading elements (say L circular elements) (FIG. 8). To compute the displacement at N stations due to the general surface loading (approximated by L circular elements), one can simply convert the problem into an equivalent primitive one: compute the displacements due to a single circular loading element at a total of L×N stations.

Figure 9:
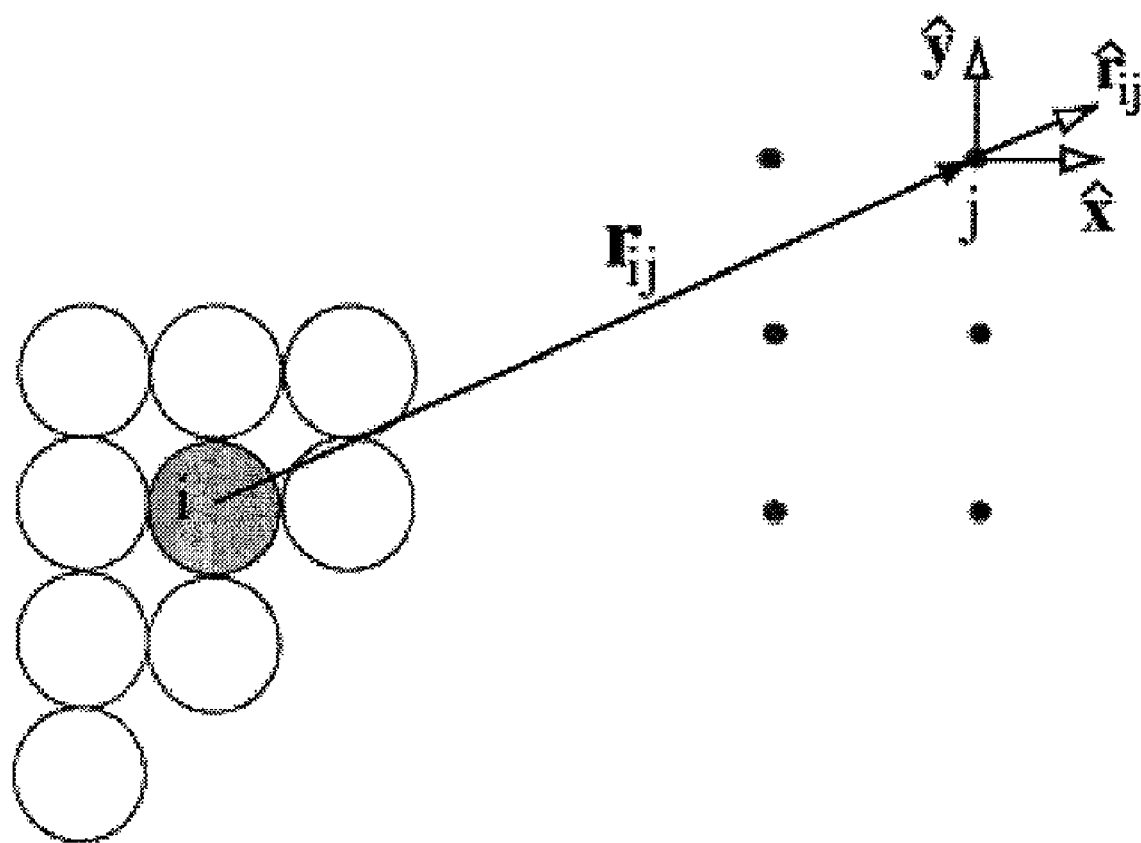
FIG. 9 is a geometric illustration of the relation between the circular loading elements i (i=1, 2, . . . , L) and the stations j (i=1, 2, . . . , N), which is used to find the equivalent or parallel problem for the k-th combination of the i-th circle and the j-th station.

According to the present invention, displacements are computed at N stations due to L circular loads (approximating an arbitrarily shaped surface loading). Each of these loads has radius a. The i-th circular load is centered at $(x_i^c, y_i^c)$ and is subject to a uniform pressure $Q_i$, (i=1, 2, . . . , L) which is considered positive if the associated force is oriented in the z-direction, i.e. into the half-space. The j-th station (j=1, 2, . . . , N) has surface coordinates $(x_j^s, y_j^s)$. Then, the relative position vector describing the position of station j relative to circle i is (FIG. 9)

$$r^{ij} = \sqrt{(x_j^s - x_i^c)^2 + (y_j^s - y_i^c)^2} \tag{29}$$

which is simply the distance from the center of load i to station j. The unit vector which points from the center of circle i to station j is $$\hat{r}^{ij} = \hat{r}_x^{ij}\hat{x} + \hat{r}_y^{ij}\hat{y} \tag{30}$$

where $$\hat{r}_x^{ij} = \frac{(x_j^s - x_i^c)}{r^{ij}} \tag{31}$$

$$\hat{r}_y^{ij} = \frac{(y_j^s - y_i^c)}{r^{ij}}.$$

Making use of the SEMI method, one can find a total of N displacement vectors (j=1, 2, . . . , N)

$$d^{ij} = d_r^{ij}\hat{r} + d_z^{ij}\hat{z} \tag{32}$$

produced by the i-th unit circular load centered at $(x_i^c, y_i^c)$. In order to obtain the response at station j due to all the circular loads (i=1, 2, . . . , L) we must transform these vectors from the local cylindrical coordinate system into the global Cartesian coordinate system, i.e. find $$d^{ij} = d_x^{ij}\hat{x} + d_y^{ij}\hat{y} + d_z^{ij}\hat{z} \tag{33}$$

for i=1, 2, . . . , L and j=1, 2, . . . , N, or, equivalently, for k=1, 2, . . . , L×N. This can be done by projecting the radial component of d onto unit vectors in the X and Y directions, i.e.

$$d_x^{ij} = d_r^{ij}\hat{r}_x^{ij} \tag{34}$$

$$d_y^{ij} = d_r^{ij}\hat{r}_y^{ij}$$

In so doing, the displacement at a given station j (j=1, 2, . . . , N) in response to the original L circular loads centered at $(x_i^c, y_i^c)$ with pressure $Q_i$ (i=1, 2, . . . , L) can be simply scaled from the unit load responses to the appropriate loads, i.e.

$$u^j = \sum_{i=1}^{L} Q_i d^{ij}. \tag{35}$$

Therefore, with the SEMI solution, Eq. (32) is first applied to find the response at station j (j=1, 2, . . . , N) due to a single unit circular load at $(x_i^c, y_i^c)$. The response is then transformed from local cylindrical coordinates into the global Cartesian coordinates via Eqs. (33) and (34). Finally Eq. (35) is utilized to find the response at station j (i=1, 2, . . . , N) due to all the discretized circular loads at $(x_i^c, y_i^c)$ with pressure $Q_i$ (i=1, 2, . . . , L).

TABLE 1

Layered Model 1: Pressure q = 1 kPa and loading radius R = 1 km.

| Layer # | Thickness (km) | Young's Modulus E (GPa) | Poisson's Ratio v |
|---|---|---|---|
| 1 | 0.5 | 5.0 | 0.3 |
| 2 | 5 | 30.0 | 0.25 |
| 3 | Infinite | 150.0 | 0.2 |

TABLE 2

Layered Model 2: Pressure q = 1 kPa and loading radius R = 1 km.

| Layer # | Thickness (km) | Young's Modulus E (GPa) | Poisson's Ratio v |
|---|---|---|---|
| 1 | 0.5 | 150.0 | 0.2 |
| 2 | 5 | 30.0 | 0.25 |
| 3 | Infinite | 5.0 | 0.3 |

TABLE 3

Number of points in different sectors (i.e., Cases I-IV) and the corresponding RMS relative errors (%) between the direct and SEMI methods for Model 1.

| | Case I | | | | Case II | | | |
|---|---|---|---|---|---|---|---|---|
| Sect | pts | $RMS_{ur}$ | $RMS_{uz}$ | $RMS_{max}$ | pts | $RMS_{ur}$ | $RMS_{uz}$ | $RMS_{max}$ |
| 1 | 13 | 3.83 | 3.28 | 3.83 | 19 | 0.323 | 0.740 | 0.740 |
| 2 | 6 | 3.98 | 1.19 | 3.98 | 11 | 0.273 | 0.0779 | 0.273 |
| 3 | 3 | 0.0796 | 0.00154 | 0.0796 | 3 | 0.0796 | 0.00154 | 0.0796 |
| Max | 20 | 3.98 | 3.28 | 3.98 | 31 | 0.323 | 0.740 | 0.740 |

| | Case III | | | | Case IV | | | |
|---|---|---|---|---|---|---|---|---|
| Sect | pts | $RMS_{ur}$ | $RMS_{uz}$ | $RMS_{max}$ | pts | $RMS_{ur}$ | $RMS_{uz}$ | $RMS_{max}$ |
| 1 | 31 | 0.0433 | 0.173 | 0.173 | 55 | 0.00597 | 0.00938 | 0.00938 |
| 2 | 21 | 0.0191 | 0.00613 | 0.0191 | 41 | 0.00208 | 0.00067 | 0.00208 |
| 3 | 4 | 0.0395 | 0.00115 | 0.0395 | 5 | 0.0216 | 0.00084 | 0.0216 |
| Max | 54 | 0.0433 | 0.173 | 0.173 | 99 | 0.0216 | 0.00938 | 0.0216 |

TABLE 4

Comparison of CPU times between direct and SEMI methods.

| | | 500 points | 1000 points | 10000 points | 100000 points |
|---|---|---|---|---|---|
| Model 1 | Direct | 24 s | 48 s | 8 m 6 s | 80 m 37 s |
| | SEMI I | <1 s | <1 s | 1 s | 3 s |
| | II | <1 s | <1 s | 1 s | 3 s |
| | III | <2 s | <2 s | 2 s | 4 s |
| | IV | <4 s | <4 s | 4 s | 7 s |
| Model 2 | Direct | 25 s | 51 s | 8 m 32 s | 84 m 37 s |
| | SEMI I | <1 s | <1 s | 1 s | 3 s |
| | II | <1 s | 1 s | 2 s | 3 s |
| | III | <2 s | 2 s | 3 s | 4 s |
| | IV | <4 s | 4 s | 5 s | 7 s |

Computer configuration: Dell Workstation PWS650, Xeon CPU 3.06 GHz, 2.0 GB RAM.

Example of SEMI Method in the form of a computer program:

```
BEGIN
Get surface circle uniform loading radius R from circular
    discretization
    Get multilayer structure information: thickness, Young's
        modulus, Poisson ratio.
    Get station number N and distance r^{ij}.
    Get expected RMS relative error.
Choose the total control point number M If larger than expected RMS error then
            Increase M point
        End if
    For total M control points
        Begin sparse evaluation
            Directly calculate the value of control points
                Numerical integral of Bessel function product
        End for loop
    Pre-calculation
            B-Spline coefficients for near-field
            B-Spline coefficients for middle-field
            Inverse B-Spline for far-field
    For total N stations
        Begin
            Judge the station belongs to which field
            Choose coefficient for the corresponding field
            Begin massive interpolation
            Output displacement components
        End for loop
END
```

According to some embodiments the process of the present invention can be applied to find the surface displacement of any of a wide variety of bodies. For example, the SEMI method can be used to find the displacement of: pavement under the load of a vehicle, the earth under a mountain or river, the earth under a building, a gasket under compression by a flange, or an o-ring under a working load. The examples set forth here are only for illustrative purposes and are not limiting. The process of the present invention can be used to predict elastic surface deformation of any surface in response to any arbitrarily shaped load regardless of the composition or size of the loading body, or that of the deforming surface.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

We claim:

1. A process for calculating surface deformation, comprising:
    a. providing a substrate having p layers;
    b. providing a load body having a contacting surface and the contacting surface is in contact with and disposed on the substrate and exerting a vertical load on the substrate;
    c. dividing the load body's contacting surface into a number L of circles each having an equal radius R;

d. choosing N stations located at the surface of the substrate;
e. selecting a desired maximum RMS relative error;
f. selecting a number M of control points for forming a B-spline curve of the surface displacement in the radial direction;
g. checking the expected error resulting from the number M of selected control points and comparing the expected error to the desired maximum RMS relative error;
h. proceeding to a next step when the expected error is equal to or less than the desired maximum RMS relative error, or selecting more control points when the expected error is greater than the desired maximum RMS relative error;
i. pre-calculating B-spline coefficients for a near field surface displacement, wherein the near field contains control points having spacing r, wherein r can have values between 0 and 2R, wherein the near field is defined by the range from 0 to 2R, wherein the near field is divided into three subsections defined by 0 to R−δ, R−δ to R+δ, and R+δ to 2R, wherein δ is between 0.02R and 0.1R, and wherein the distance between each control point within the first and third subsections is graded so that $|r_{i+1}-r_i|=g|r_i-r_{i-1}|$ and wherein g is between 1 and 2;
j. pre-calculating B-spline coefficients for a middle field surface displacement, wherein the middle field contains control points having spacing r, wherein r can vary from 2R to 40R, wherein the control points are uniformly distributed in the middle field by a spacing defined according to the natural logarithmic function ln(r);
k. pre-calculating inverse B-spline coefficients for a far field, wherein the far field contains control points having spacing 1/r, wherein r can vary from 40R to 100R, wherein the control points are uniformly distributed according to the function 1/r;
l. selecting coefficients and inverse coefficients from the pre-calculated coefficients and inverse coefficients, and forming a B-spline therefrom;
m. interpolating according to the B-spline; and
n. calculating station displacement for each station.

2. The process of claim 1 wherein the layered surface is a pavement.

3. The process of claim 1 wherein the layered surface is an earth structure.

4. The process of claim 1 wherein the layered surface is a foundation structure.

* * * * *